United States Patent [19]

Yamashita

[11] Patent Number: 4,699,766
[45] Date of Patent: Oct. 13, 1987

[54] AUTOMATIC CHEMICAL ANALYZER

[75] Inventor: Kiyoshi Yamashita, Ootawara, Japan

[73] Assignee: Kabushiki Kaisha Toshiba, Kawasaki, Japan

[21] Appl. No.: 867,920

[22] Filed: May 29, 1986

[30] Foreign Application Priority Data

May 30, 1985 [JP] Japan .................. 60-118635

[51] Int. Cl.4 ............................. G01N 35/04
[52] U.S. Cl. .............................. 422/64; 356/440;
422/67; 436/48
[58] Field of Search ............ 422/63, 64, 67; 436/48;
356/440

[56] References Cited

U.S. PATENT DOCUMENTS 3,484,206 12/1969 Loebl ........................... 422/64
4,276,258 6/1981 Ginsberg et al. .................. 422/64

FOREIGN PATENT DOCUMENTS 3306491 9/1983 Fed. Rep. of Germany ........ 422/64
3504955 8/1985 Fed. Rep. of Germany ........ 422/67
58-30651 2/1983 Japan ........................... 422/67
184535 10/1983 Japan .
60-4861 1/1985 Japan ........................... 422/64

Primary Examiner—Michael S. Marcus
Attorney, Agent, or Firm—Oblon, Fisher, Spivak, McClelland & Maier

[57] ABSTRACT

An automatic chemical analyzer comprises a first rotating table supporting a plurality of reaction tubes along a circular first arrangement line and adapted to be intermittently rotated by a first drive motor, and a second rotating table supporting another plurality of reaction tubes along a circular second arrangement line concentric with the first arrangement line and adapted to be intermittently rotated in synchronism with the first table by a second drive motor. The reaction tubes are transferred between the first and second tables. A sampling nozzle, a diluent nozzle, and a plurality of reagent nozzles are fixedly arranged right over the reaction tubes supported by the first and second tables. A specimen, diluent and reagents are injected into the reaction tubes through the nozzles. The absorbance or other property of mixtures of the specimen, diluent and reagents are measured by a measuring system whose measuring point moves along the second arrangement line.

6 Claims, 3 Drawing Figures

AUTOMATIC CHEMICAL ANALYZER

BACKGROUND OF THE INVENTION

The present invention relates to an automatic chemical analyzer for quickly analyzing a plurality of specimens or items in succession.

Automatic chemical analyzer are apparatuses which are used to examine and analyze specimens, such as urine or blood, extracted from the human body or the like. In many of recently developed analyzers of this type, urine, blood or other specimens is put into a plurality of reaction tubes, and a plurality of kinds of reagents are distributed into the tubes so that the specimen reacts with the reagents. Thereafter, the absorbance or other property of the resulting solutions is measured.

In one such prior art automatic chemical analyzer, first and second reaction sections are arranged adjacent to each other. In the first reaction section, a first rotating table supports a number of reaction tubes along a circular first arrangement line. A first drive motor rotates the first table so that the tubes move intermittently along the first arrangement line. A sampling mechanism injects the speciment into the reaction tubes, while a first reagent distributing mechanism distributes a first reagent into the tubes. A washer-drier portion serves to wash and dry the tubes. In the second reaction section, a second rotating table supports a number of reaction tubes along a circular second arrangement line. A second drive motor rotates the second table so that these tubes move in synchronism with those in the first reaction section. A second reagent distributing mechanism distributes a second reagent into the tubes. A measuring system optically measures the absorbance or other property of mixtures of specimen and reagents in the tubes. The reagent tubes are transferred between the first and second reaction sections.

Constructed in this manner, the conventional apparatus has the following three problems. First, the first and second arrangement lines have only one reagent distributing station each. Therefore, the reagent distributing mechanisms are provided with distributing nozzles which are movable between the distributing stations and a reagent repository. In distributing the reagents in accordance with the purpose of mesurement, desired reagents in the repository are indexed and injected into the reaction tubes via the distributing stations. Thus, the distributaing mechanisms are complicated and the reagent indexing takes too much time for the measurement to be accomplished quickly.

Secondly, the measuring point of the measuring system is fixed at one position on the second arrangement line. Accordingly, the reaction tubes on the second line must be transported to the measuring point in every measurement. During the transport, distribution of other reagents or other processing cannot be carried out, so that a speedy measurement is impossible.

Thirdly, since the first and second reaction sections adjoin each other, the whole appartus body is inevitably bulky.

The second problem can be solved by the technique disclosed in Japanese Patent Disclosure No. 4535/83, in ehich the measuring point is moved in the direction of arrangement of reaction tubes. The first and third problems have yet to be solved.

SUMMARY OF THE INVENTION

The object of the present invention is to provide an automatic chemical analyzer which is improved in measuring speed and reduced in overall size, and in which supply means is simple in construction.

According to the invention, there is provided an automatic chemical analyzer, which comprises first support means for supporting a plurality of vessels along a circular arrangement line, second support means for supporting another plurality of vessels along a second circular arrangement line concentric with the first arrangement line, first drive means for driving the first support means so that the vessels supported by the first support means move along the first arrangement line, and for driving the second suport means so that the vessels supported by the second support means move along the second arrangement line, transfer means for transferring the vessels between the first and second support means, supply means for feeding substance into the vessels, the supply means including a plurality of nozzles fixedly arranged along at least one of the two arrangement lines, the nozzles individually feeding different kinds of substance into the vessels, and means for measuring a predetermined property of the substance in the vessels, the measuring means having a measuring point which can move along the first or second arrangement line.

In the automatic chemical analyzer according to the invention, the nozzles are fixed and therefore require neither mechanisms not time for their transport, thus permitting a speedy measurement.

Since the measuring point of the measuring system moves along the first or second arrangement line, the vessels need not be transported to the point, and some other proc essing, such as distribution of another reagent, stirring, or washing and drying, can be executed in parallel with the measurement by the measuring system. Thus, the operation is further speeded up as a whole. Moreover, the measurement and other processes can enjoy necessary and suficient time each. Furthermore, measurement data on each vessel can be obtained wherever the vessel is located, so that the progress of reaction in the vessel can be grasped with accuracy.

Since the first and second arrangement lines are concentric, the apparatus can be reduced in overall size.

DETAILED DESCRIPTION OF THE PREFERRED EMBODIMENTS

Figure 1:
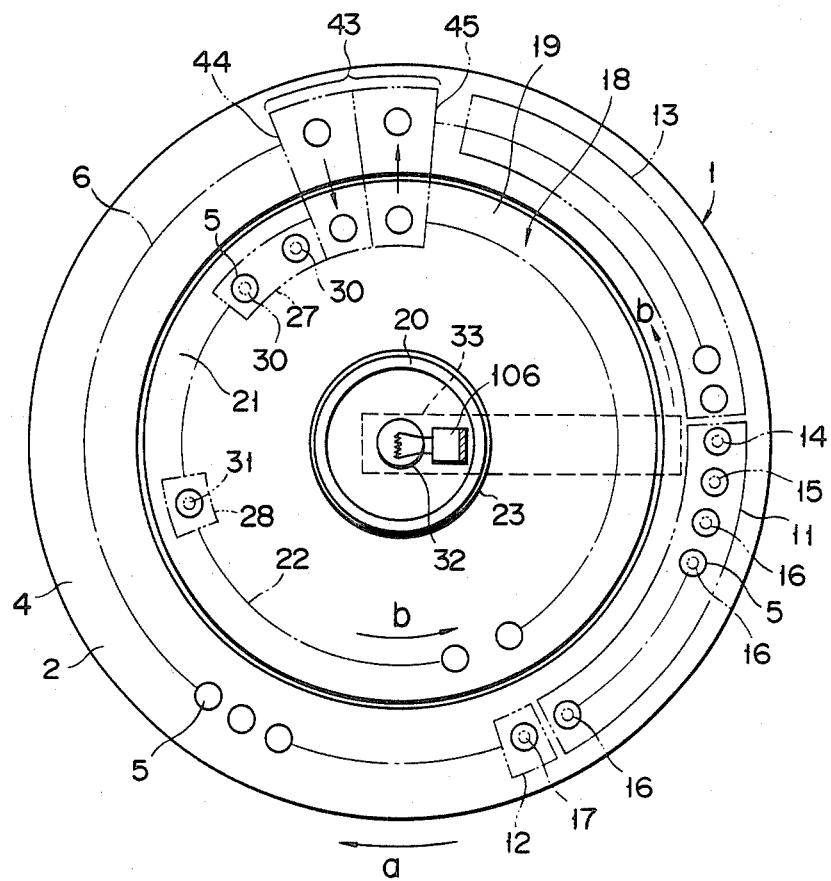
FIG. 1 is a plan view schematically showing an automatic chemical analyzer according to an embodiment of the present invention.
Figure 2:
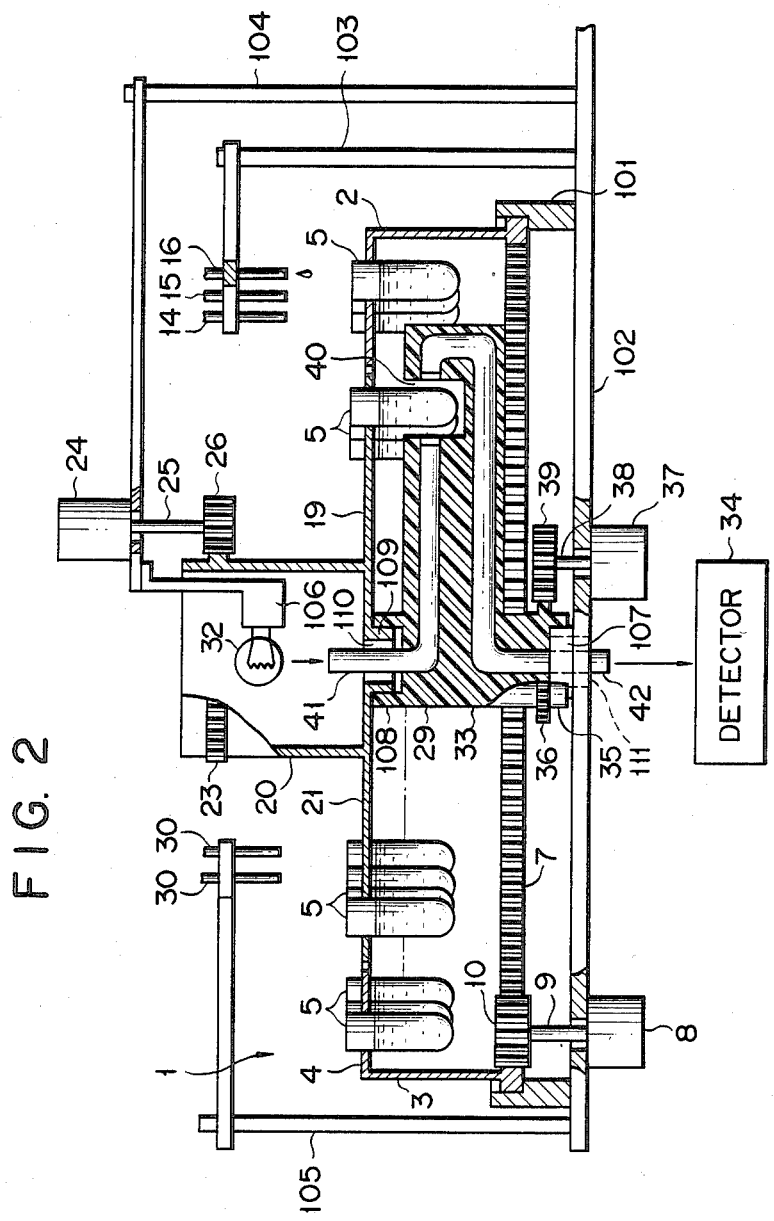
FIG. 2 is a vertical sectional view of the analyzer shown in FIG. 1.

In FIGS. 1 and 2, numeral 1 designates a first reaction section. Section 1 comprises first rotating table 2 which includes lage-diameter cylindrical member 3 and ring-shaped holder 4 connected integrally to the inner periphery of the top end of member 3. The bottom end of cylindrical member 3 is rotatably supported on base 102 by first support member 101. Holder 4 supports a plurality of reaction tubes 5 which are arraanged a first circular ararangement line 6 around the center of rotation of table 2. Internal teeth 7 are formed at the lower portion of the inner periphery of member 3. They are in mesh with gear 10 which is mounted on shaft 9 of first drive motor 8. Motor 8, which is mounted on base 102, serves to rotate table 2 intermittently in the direction of arrow a.

First reaction section 1 further comprises first distributor portion 11, first stirrer portion 12, and washer-drier portion 13. Portion 11 includes sampling nozzle 14 for injecting a specimen or object of analysis, such as uringe or blood, into reaction tubes 5, diluent nozzle 15 for injecting a diluent into the tubes, and a plurality of first reagent nozzles 16 for distributing first reagents for a plurality of items into the tubes. Nozzles 14, 15 and 16 are fixedly supported on base 102 by second support member 103, arranged along first arrangement line 6 in the order named. These nozzles are located right over the stop positions of their corresponding reaction tubes 5 being transported intermitenly. First stirrer portion 12 includes stirrer 17 adapted to penetrate tubes 5 to stir the contents thereof. Stirrer 17 is disposed over the stop positon of that tube 5 which is located on that portion of line 6 just behind first distributor portion 11, with respect to the advancing direction of tubes 5, and is advancing intermittently. The stirrer can move up and down, controlled by a first lift mechanism (not shown). Washer-drier portion 13 is arranaged ahead of portion 11 along line 6, and serves to wash and dry the reacion tubes.

Second reaction section 18 is disposed inside first reaction section 1. It comprises second rotating table 19 which can rotate about the center of rotation of first rotating table 2. Table 19 includes small-diameter cylindrical member 20 and disk-shaped holder 21 connected integrally to the bottom end of member 20. Holder 21, which is disposed inside and flush with ring-shaped holder 4, supports a plurality of reaction tubes 5 which are arranged along a second circular arrangement line 22 concentric with first arrangement line 6. External teeth 23 are formed at the upper portion of the outer periphery of member 20. They are in mesh with gear 26 which is mounted on shaft 25 of second drive motor 24. Motor 24, which is supported on base 102 by third support member 104, serves to rotate second table 2 intermitttently, in synchronism with first table 2, in the direction of arrow b opposite to the direction of arrow a.

Second reaction section 18 further comprises second distributor portion 27, second stirrer portion 28, and measuring system 29. Portion 27 includes a plurality of second reagent nozzles 30 for distributing second reagents for a plurality of items into tube 5. Nozzles 30 are fixedly supported on base 102 by fourth support member 105, arranged along second arrangement line 22. These nozzles are located right over the stop positions of their corresponding reaction tubes 5 being transported intermittently. Second stirrer portion 28 includes stirrer 31 adapted to penetrate tubes 5 to stir the contents thereof. Stirrer 31 is disposed over the stop position of tube 5 which is located on that portion of line 22 behind second distributor portion 27, with respect to the advancing direction of tubes 5, and is advancing intermittently. The stirrer can move up and down, controlled by a second lift mechanism (not shown). Measuring system 29 includes light source 32, rotating optical member 33, and light detector 34 thereunder. Source 32 is supported on third support member 104 of second rotating table 19 by fifth support member 106 so as to be located at the central portion of member 20. Optical member 33 can rotate about the center of rotation of first roatating table 2 in large-diameter cylindrical member 3 of table 2. It has circular projection 35 which protrudes downward along its axis of rotation. The lower end portion of projection 35 is supported on base 102 by sixth support member 107 so that member 33 is rotatable. External teeth 36 are formed on the outer peripheral surface of projection 35. They are in mesh with gear 39 which is mounted on shaft 38 of third drive motor 37. Motor 37, which is supported on base 102, serves to rotate optical member 33 in the same direction as second table 19 or in the direction of arrow b. Groove 40 is formed in that portion of member 33 distant from its center of rotation. The bottom portion of each reaction tube 5 held by table 19 can pass through groove 40. First and second optical fibers 41 and 42 are buried in rotating optical member 33. One end of first optical fiber 41 projects upward from the central portion of member 33, penetrating center hole 110 of table 19 to face light source 32. The other end of fiber 41 faces groove 40. One end of second optical fiber 42 faces groove 40 so as to be opposite to the other end of fiber 41. The other end of fiber 42 projects downward from the central portion of member 33, penetrating hole 111 in base 102 to face light detector 34. A light beam from light source 32 is radiated toward reaction tube 5 in groove 40 through first optical fiber 41. After it is transmitted through tube 5, the light beam passes through second optical fiber 41 and is received by detector 34. Thereupon, the beam is converted into an electrical signal by detector 34. Rotating optical member 33 has cylindrical projection 108 which protrudes upward along its axis of rotation. Fitted in projection 108 is cylindrical projection 109 which protrudes downward from second table 19 along the axis of rotation thereof. Thus, table 19 is supported for rotation.

Numeral 43 designates a reaction tube transfer mechanism for transferring reaction tubes 5 between first and second reaction sections 1 and 18. Mechanism 43 includes first and second transport mechanisms 44 and 45. First transport mechanism 44 delivers tubes 5 passed through first stirrer portion 12 of section 1 to a stage just in front of second distributor portion 27 of section 18. Second transport mechanism 45 delivers tubes 5 fed past second stirrer portion 28 of section 18 to a stage just ahead of washer-drier portion 13 of section 1. Mechanisms 44 and 45 first grip and raise tube 5, transport it horizontally, and then lower and release it.

The operation of the apparatus with the aforementioned construction will now be described.

First, when reaction tube 5 is located right under sampling nozzle 14, the specimen is injected into the tube through nozzle 14. When the tube is then located just under diluent nozzle 15, the diluent is injected into the tube through nozzle 15. Thereafter, tube 5 moves under first reagent nozzles 16 in succession. When it is positioned right under a predetermined on of nozzles 16, a reagent for apredetermined item is distributed into the tube through the first reagent nozzle. Subsequenetly, when tube 5 is located right under first stirrer 17, the stirrer lowers to penetrate the tube, and stirs the specimen, diluent and first reagent in the tube. Then, the tube is moved to first transport mechanism 44 while the specimen tis reacting to the reagent, and delivered to second reaction section 18 by mechanism 44. Thereafter, reaction tube 5 moves under second reagent nozzles 30 in succession. When it is positioned right under a predetermined one of nozzles 30, another reagent for another predetermined item is distributed into the tube through the second reagent nozzle. When tube 5 is then located right under second stirrer 31, the stirrer lowers to penetrate the tube, and stirs the specimen, diluent, and first and second reagents in the tube.

After the specimen, diluent, and first and second reagents are distributed and stirred in this manner, reaction tube 5 moves toward second transport mechanism 45 along second arrangement line 2. During this movement, reaction between specimen and reagents proceeds in the tube. After a predetermined time of reaction in the moving tube, rotating optical member 33 is rotated and light source 32 is turned on while the tube is at a standstill. When the central portion of tube 5 is positioned exactly on an optical path in groove 40, the absorbance or other property of the contents of the tube is measured.

After the measurement, reaction tube 5 moves to second transport mechanism 45 along second arrangement line 22, and is delivered to first reaction section 1 by mechanism 45. Then, it is washed and dried at washer-drier portion 13, and subjected to a measurement in the next stage.

These operations, in a series, are repeated for the several reaction tubes.

According to the arrangement described above, nozzles 14, 15, 16 and 30 of first and second distributor portions 11 and 27 are located right over reaction tubes 5. Therefore, they require neither mechanisms nor time for their transport, permitting a speedy measurement.

Since the measuring point of measuring system 29 moves along second arrangement line 22, reaction tubes 5 need not be transported to it, and some other processing, such as distribution of another reagent, stirring, or washing and drying, can be executaed in parallel with the measurement by system 29. Thus, the operation is further speeded up as a whole. Moreover, the measurement and other processes can enjoy necessary and sufficient time each. Furthermore, measurement data on each reaction tube 5 can be obtained with every intermittent shifting of its positon, so that the progress of the reaction in the tube can be grasped with accuracy.

Since first and second reaction sections 1 and 18 are arraanged concentrically, the apparatus can be reduced in overall size.

Figure 3:
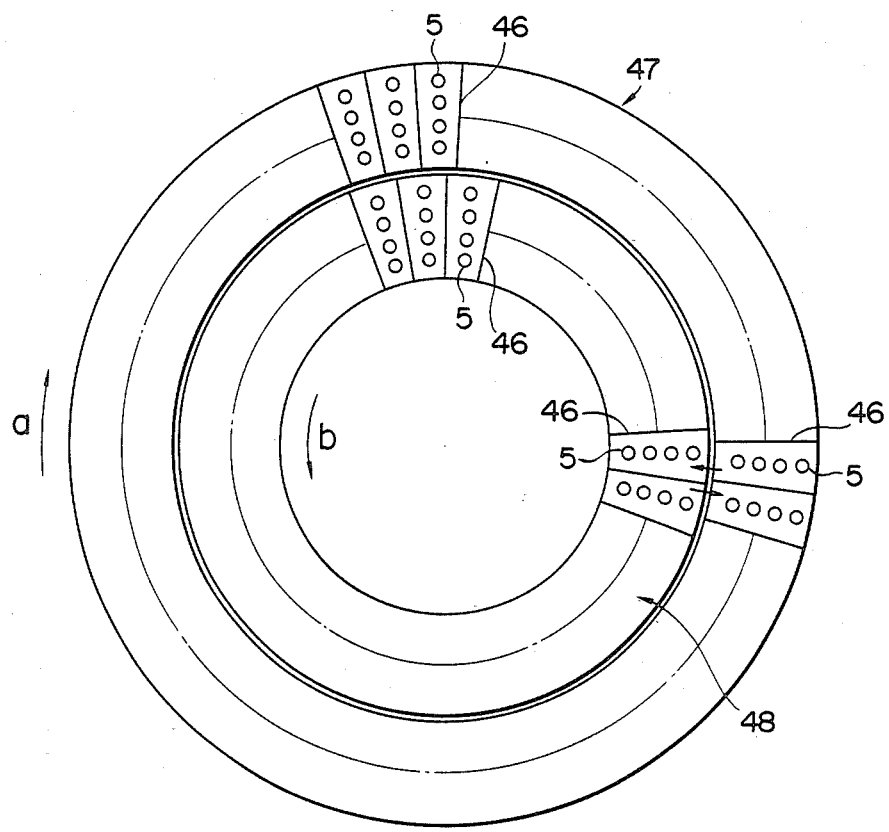
FIG. 3 is a plan view schematically showing an automatic chemical analyzer according to another embodiment of the invention.

FIG. 3 shows an outline of an automatic chemical analyzer according to another embodiment of the present invention. This analyzer comprises first reaction section 47 including a number of reaction tube cassettes 46 of the same configuration containing, for example, four reaction tubes 5 each and arranged in a circle, and second reaction section 48 including a number of reaction tube cassettes 46 arranged in a circle concentric with section 47. Cassettes 46 are transferred between reaction sections 47 and 48.

This apparatus performs the same operations as the one shown in FIGS. 1 and 2. Having reaction tube cassettes 46 each containing a plurality of reaction tubes 5, moreover, the analyzer of this embodiment is suited for the case where measurement data for a multitude of items are required.

The present invention is not limited to the embodiments described above. For example, a plurality of sampling nozzles may be provided so that a plurality of kinds of specimens are distributed into reaction tubes. The measurement can be accomplished more effectively by arranging the reagent nozzles according to priority based on reaction time.

What is claimed is:

1. An automatic chemical analyzer comprising:
   first support means for supporting a plurality of vessels along a first circular arrangement line;
   second support means for supporting another plurality of vessels along a second circular arrangement line concentric with the first circular arrangement line, one of said first and second circular arrangement lines being within the other of said first and second circular arrangement lines;
   first drive means for driving the first support means so that vessels supported by the first support means move along the first circular arrangement line, and for driving the second support means so that vessels supported by the second support means move along the second circular arrangement line;
   transfer means for transferring vessels between the first and second support means;
   supply means for feeding substances into vessels supported on at least one of said first and second support means, said supply means including a plurality of nozzles fixedly arranged along at least one of the two circular arrangement lines, said nozzles individually feeding different kinds of substances into vessels supported on at least one of said first and second support means; and
   means for measuring a predetermined property of substances which have been fed in vessels in at least one of the first and second arrangement lines by said supply means, said measuring means having a measuring point which can move along said one circular arrangement line.

2. The automatic chemical analyzer according to claim 1, wherein said first support means is a doughnut-shaped first rotating table, and said second support means is a second rotating table disposed inside the first table.

3. The automatic chemical analyzer according to claim 1, wherein said first drive means includes first intermittent drive means for driving the first support means so that the vessels supported by the first support means move intermittently, and second intermittent drive means for driving the second support means so that the vessels supported by the second support means move intermittently in synchronism with the vessels supported by the first support means.

4. The automatic chemical analyzer according to claim 1, wherein said plurality of nozzles includes a sampling nozzle for injecting a specimen into vessels supported on one of said first and second support means, a diluent nozzle for injecting a diluent into vessels supported on at least one of said first and second support means, and a plurality of reagent nozzles for individually injecting a plurality of reagents into vessels supported on one of said first and second support means.

5. The automatic chemical analyzer according to claim 1, wherein said measuring means includes a rotating member and second drive means for driving the rotating member, said rotating member having a center of rotation on the center of the first circular arrangement fine and said measuring point at a position corresponding to one of the first and second circular arrangement lines.

6. The automatic chemical analyzer according to claim 1 wherein said plurality of nozzles is mounted in a fixed position.

* * * * *